United States Patent
Boynton et al.

(10) Patent No.: US 7,422,576 B2
(45) Date of Patent: Sep. 9, 2008

(54) LOCALIZED LIQUID THERAPY AND THERMOTHERAPY DEVICE

(75) Inventors: Thomas A. Boynton, Floresville, TX (US); Royce Johnson, Universal City, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 10/320,211

(22) Filed: Dec. 16, 2002

(65) Prior Publication Data

US 2003/0225441 A1 Dec. 4, 2003

Related U.S. Application Data

(63) Continuation of application No. 09/590,333, filed on Jun. 8, 2000, now Pat. No. 6,520,982.

(51) Int. Cl.
*A61F 7/00* (2006.01)
*A61F 7/02* (2006.01)

(52) U.S. Cl. .................. 604/291; 602/41; 607/104

(58) Field of Classification Search .............. 607/96, 607/98, 99, 104, 108, 109–112; 601/159–162; 604/319–323, 304–305, 291; 602/41–48
See application file for complete search history.

(56) References Cited

U.S. PATENT DOCUMENTS

| | | | |
|---|---|---|---|
| 1,355,846 A | 10/1920 | Rannells | |
| 2,272,481 A | * 2/1942 | Rinkes et al. | ................ 601/166 |
| 2,547,758 A | 4/1951 | Keeling | |
| 2,632,443 A | 3/1953 | Lesher | |
| 2,682,873 A | 7/1954 | Evans et al. | |
| 2,969,057 A | 1/1961 | Simmons | |
| 3,367,332 A | 2/1968 | Groves | |
| 3,520,300 A | 7/1970 | Flower | |
| 3,648,692 A | 3/1972 | Wheeler | |
| 3,682,180 A | 8/1972 | McFarlane | |
| 3,826,254 A | 7/1974 | Mellor | |

(Continued)

FOREIGN PATENT DOCUMENTS

AU     550575 A1    8/1982

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery, . . . .

(Continued)

*Primary Examiner*—Roy D Gibson

(57) ABSTRACT

A device for directly applying thermotherapeutic liquid to an area upon the surface of an afflicted patient, and methods of use thereof, are described. In particular a device for applying water-based liquid at a therapeutic temperature directly to an afflicted area in order to create a localized hyperthermia, is presented. The afflicted area may be either on the skin of the patient, or subcutaneous. The device is also effective for disinfection, irrigation, lavage, and the like, when employing a suitable solution. The liquid may also have a mild oxidizing effect, which, if greater upon afflicted than upon non-afflicted cells, would enhance the therapeutic effect in conjunction with the therapy herein described.

20 Claims, 7 Drawing Sheets

U.S. PATENT DOCUMENTS

| | | | |
|---|---|---|---|
| 4,080,970 A | 3/1978 | Miller | |
| 4,096,853 A | 6/1978 | Weigand | |
| 4,112,947 A * | 9/1978 | Nehring | 604/30 |
| 4,139,004 A | 2/1979 | Gonzalez | |
| 4,165,748 A | 8/1979 | Johnson | |
| 4,192,297 A * | 3/1980 | Labrecque | 601/166 |
| 4,233,969 A | 11/1980 | Lock et al. | |
| 4,245,630 A | 1/1981 | Lloyd et al. | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,353,359 A * | 10/1982 | Milbauer | 601/166 |
| 4,373,519 A | 2/1983 | Errede et al. | |
| 4,382,441 A | 5/1983 | Svedman et al. | |
| 4,392,853 A | 7/1983 | Muto | |
| 4,392,858 A | 7/1983 | George et al. | |
| 4,419,097 A | 12/1983 | Rowland | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vailancourt | |
| 4,540,412 A | 9/1985 | Van Overloop | |
| 4,543,100 A | 9/1985 | Brodsky | |
| 4,551,139 A | 11/1985 | Plaas et al. | |
| 4,569,348 A | 2/1986 | Hasslinger | |
| 4,595,008 A | 6/1986 | Guibert | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,945,901 A * | 8/1990 | Burcke, Jr. | 601/157 |
| 4,953,565 A | 9/1990 | Tachibana et al. | |
| 4,969,880 A | 11/1990 | Zamierowski | |
| 4,979,938 A | 12/1990 | Stephen et al. | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,195,965 A | 3/1993 | Shantha | |
| 5,232,453 A | 8/1993 | Plass et al. | |
| 5,241,953 A * | 9/1993 | Sykes | 601/166 |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,458,596 A | 10/1995 | Lax et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,683,438 A | 11/1997 | Grahn | |
| 5,735,833 A | 4/1998 | Olson | |
| 6,071,267 A | 6/2000 | Zamierowski | |
| 6,135,116 A | 10/2000 | Vogel et al. | |
| 6,200,292 B1 | 3/2001 | French et al. | |
| 6,345,623 B1 | 2/2002 | Heaton et al. | |
| 6,406,447 B1 * | 6/2002 | Thrash et al. | 601/160 |
| 6,458,109 B1 * | 10/2002 | Henley et al. | 604/304 |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,800,074 B2 * | 10/2004 | Henley et al. | 604/319 |
| 6,814,079 B2 | 11/2004 | Heaton et al. | |
| 7,144,390 B1 | 12/2006 | Hannigan et al. | |
| 2002/0115951 A1 | 8/2002 | Norstream et al. | |
| 2002/0120185 A1 | 8/2002 | Johnson | |
| 2002/0143286 A1 | 10/2002 | Tumey | |

FOREIGN PATENT DOCUMENTS

| | | |
|---|---|---|
| AU | 745271 | 3/2002 |
| AU | 755496 | 12/2002 |
| CA | 2005436 | 6/1990 |
| DE | 26 40 413 A1 | 3/1978 |
| DE | 43 06 478 A1 | 9/1994 |
| DE | 295 04 378 U1 | 9/1995 |
| EP | 0117632 A2 | 1/1984 |
| EP | 0100148 | 2/1984 |
| EP | 0161865 | 11/1985 |
| EP | 0358 302 | 3/1990 |
| EP | 1 018 967 B1 | 8/2004 |
| GB | 692578 | 6/1953 |
| GB | 2 197 789 A | 6/1988 |
| GB | 2333965 A | 8/1999 |
| GB | 2329127 B | 8/2000 |
| SG | 71559 | 4/2002 |
| WO | WO 80/02182 | 10/1980 |
| WO | WO 93/09727 | 5/1993 |
| WO | WO/94/20041 | 9/1994 |
| WO | WO 96/05873 | 2/1996 |
| WO | WO 97/18007 | 5/1997 |
| WO | WO 99/13793 | 9/1998 |
| WO | WO-00/07653 | 2/2000 |

OTHER PUBLICATIONS

Susan Mendez-Eastman, RN; When Wounds Won't Heal, RN Jan. 1998, Volume 61(1); Medical Economics Company, Inc., Montvale, NJ, USA.

James H. Blackburn, II, MD. et al; Negative-Pressure Dressings as a Bolster for Skin Grafts; Annals of Plastic Surgery, vol. 40, No. 5, May 1998, pp. 453-457; . . . .

John Masters; Letter to the editor; Britsh Journal of Plastic Surgery, 1998, vol. 51(3), p. 267; Elsevier Science/The British Association of Plastic Surgeons, UK.

S.E. Greer, et al; The Use of Subatmospheric Pressure Dressing Therapy to Clos Lymphocutaneous Fistulas of the Groin; British Journal of Plastic Surgery (2000), 53 . . . .

George V. Letsou, M.D., et al; Stimulation of Adenylate Cyclase Activity in Cultured Endothelial Cells Subjected to Cyclic Stretch; Journal of Cardiovascular Surgery, 31, 1990.

PCT International Search Report; PCT international application PCT/GB98/02713; Jun. 8, 1999.

PCT Written Opinion; PCT international application PCT/GB98/02713; Jun. 8, 1999.

PCT International Examination and Search Report, PCT international application PCT/GB96/02802; Jan. 15, 1998 and Apr. 29, 1997.

PCT Written Opinion, PCT international application PCT/GB/96/02802; Sep. 3, 1997.

Kostyuchenok, B.M, et al. ;Vacuum Treatment in the Surgical Management of Purulent Wounds; Vestnik Khirurgi, Sep. 1986.

Davydov, Yu. A., et al; Vacuum Therapy in the Treatment of Purulent Lactation Mastitis; Vestnik Khirurgi, Sep. 1986.

Yusupov, Yu. N., et al; Active Wound Drainage, Vestnik Khirurgi, vol. 138, Issue 4, 1987.

Davydov, Yu. A., et al; Bacteriological and Cytological Assessment of Vacuum Therapy of Purulent Wounds; Vestnik Khirurgi, Oct. 1988.

Davydov, Yu. A., et al; Concepts For the Clinical-Biological Management of the Wound Process in the Treatment of Purulent Wounds by Means of Vacuum Therapy; Vestnik Khirurgi.

International Search Report for PCT international application PCT/GB95/01983; Nov. 23, 1995.

Patent Abstract of Japan; JP4129536; Terumo Corporation; Apr. 30, 1992.

Orringer, Jay, et al., "Management of Wounds in Patients with Complex Enterocutaneous Fistulas", Surgery, Gynecology & Obstertics, Jul. 1987, V. 165, pp. 79-80.

\* cited by examiner

LOCALIZED LIQUID THERAPY AND THERMOTHERAPY DEVICE

RELATED APPLICATIONS

This application is a continuation of U.S. application Ser. No. 09/590,333, filed Jun. 8, 2000 now U.S. Pat. No. 6,520, 982. By this reference, the full disclosure of U.S. application Ser. No. 09/590,333 is incorporated herein as though fully set forth in their respective entirety.

FIELD OF THE INVENTION

This invention relates generally to devices for applying localized liquid therapy and/or thermotherapy to an afflicted area of a patient. More particularly, this invention relates to a device, and method of use thereof, which directly applies a liquid, most usually a water based liquid to a selected area to create the desired therapeutic effect, most usually a localized hyperthermia, which is effective in treating localized afflictions, such as moles, lesions, tumors, malignancies, both surface and subcutaneous, and the like, or a therapeutic lavage or irrigation.

BACKGROUND OF THE INVENTION

Heat and cold have both been used to effectively treat afflicted patients. Directly applying liquid to afflicted cells is also well known. Cold has often been used as a localized treatment, while heat has been, and is currently used as both a localized and total body treatment. Using heat to treat a localized afflicted area of an afflicted patient is most relevant to the present invention.

The search continues for ways to effectively treat wounds, tumors and similar disorders while minimizing adverse collateral effects. For example, assignee has been a leader in treating open wounds through a process known as Vacuum Assisted Closure™, ("V.A.C.®"). In a similar vein, localized thermotherapy, primarily localized hyperthermia, has also shown promise as a treatment modality which is capable of producing beneficial therapeutic effects without significant adverse collateral effects for certain conditions. However, the localized hyperthermic treatment modalities in the prior art, all suffer from serious drawbacks, limitations, or side effects.

Research has demonstrated that heating cancerous, or other abnormal cells to over about 42° Celsius ("C.") can kill the abnormal cells, while causing little damage to the surrounding normal cells. This treatment is temperature sensitive. Heating the cancer cells, for example, to a temperature between nominal body temperature, 37° C. and approximately 41° C. or greater can seriously damage them. To maximize patient safety, this hyperthermia treatment must be localized.

The variety of available heat transfer methods for localized thermotherapy is limited. Heat is transferred in three ways, radiation, convection, or conduction. The heat transfer medium creating the localized hyperthermia can be either heated in situ or be heated exogenously, before being placed upon the patient. The medium can either be placed in direct contact with the afflicted cells or, transfer heat to the afflicted cells through an intermediary.

Localized hyperthermia therapy is presently used in treating prostate afflictions, breast cancer, and other afflictions. This modality involves placing implants about the afflicted patient's afflicted cells, and then heating the implants by radiating EMF or ultrasonic energy thereto. The heat from the implants then migrates into the afflicted tissue, via conduction, thereby raising the temperature of the afflicted cells.

Several issued patents demonstrate variations of this technique. Issues relating to possible adverse affects of exposure to both radiation, and radiated energy abound. However, as most sufferers of prostate cancer are older men who are past the age of fathering children, and female breasts are relatively remote from the female reproductive organs, the possible long-term adverse collateral effects of using such radiant energy treatments are minimized.

Applicant has discovered various patents that employ and exemplify other energy transfer methods and media in creating localized hyperthermias. The first of these patents, Guibert, U.S. Pat. No. 4,595,008, issued Jun. 17, 1986, may be summarized as follows:

" . . . air heated to a temperature well above normal body temperature is projected as a high velocity stream in a pulsatory wave pattern toward a localized skin area overlying a problem region, thereby subjecting this area to high-velocity heated air pulses separated by lower air temperature, relatively static intervals.

"The pulsatory wave pattern is created by apparatus, which operates in a periodic interruption mode, in a cyclical stepping mode or in a cyclical sweeping mode, depending on the nature of the instrument and its intended applications.

"As a consequence of the pulsatory wave pattern, heat transfer takes place through the body tissue toward the problem region during the intervals between the pulses, this inward transfer acting to reduce the temperature at the skin surface to a degree preventing an undue rise thereof. While during the pulse periods the temperature of the hot air at the skin surface is much higher than body temperature, the duration of each pulse is relatively short and insufficient to cause discomfort or injury to the patient." Guibert Col. 2 line 61-Col. 3 line 15.

This description shows that Guibert uses a heated fluid to indirectly transfer heat to an afflicted area of a patient; the fluid, air, does not come into contact with the afflicted area. Another device that also uses a heated fluid to treat an afflicted portion of a patient's body is Shantha, U.S. Pat. No. 5,195, 965 issued Mar. 23, 1993. Shantha may be summarized as follows:

" . . . the present invention comprises an apparatus for heating the interior surfaces of a hollow organ or orifice, for example the interior surfaces of the reproductive tract of a female human being, for the treatment of viral infections and cancers. For example, the invention is useful for the treatment of Human Papilloma Virus, chlamydia, trichomonas vaginitis, vaginal yeast infections, gonococcus, rectal and anal infections, rectal and anal cancers, esophageal cancer, etc. The apparatus comprises an insertion body having a flexible outer surface and is adapted for insertion into the hollow organ or orifice, such as the female reproductive tract. The insertion body is adapted to contact and conform to the interior surfaces of the hollow organ. The apparatus also includes means for heating the outer surface of the insertion body and for maintaining a selected temperature at the outer surface.

"Preferably, the insertion body comprises an inflatable outer membrane or balloon supported about a semi-rigid support member. The inflatable balloon is adapted to contain liquid under pressure and the apparatus includes means for circulating liquid between the inflatable balloon and an external heating device. Sensor means are positioned along the outer surface of the inflatable balloon for determining the temperature of the outer surface of the balloon. Control means, responsive to the temperature of the outer surface as determined by the sensor means, are provided for controlling the external heating device so as to maintain the temperature of the outer surface at the selected temperature.

"With this construction, the inflatable balloon can be inserted into the hollow organ in an uninflated state and subsequently inflated with liquid under pressure. The liquid is then circulated and heated in the external heating device. The liquid, preferably water, is maintained at a temperature of between 40° C. and 44° C. for between 2 and 6 hours. Preferably, the water is maintained at a temperature of 41.8° C. (roughly 107.2° F.), and the inflatable body is maintained in the hollow organ for four (4) hours kills many bacteria, viruses and cancer cells. The immune system of the patient normally is stimulated by the destroyed virus cells, microbes, and cancer cells and attacks any infected or cancerous cells not destroyed by the heat. This temperature of 41.8 degree C. is low enough that healthy tissues survives relatively undamaged, owing to the lesser heat sensitivity of healthy cells as compared with infected and cancerous cells. The localized nature of the treatment, together with the relatively low temperature involved, ensures that the risk of death to the patient from an elevated body temperature is substantially zero. The rather low temperatures involved also protect the patient from much pain and discomfort during treatment." Shantha Col. 2., line 36-Col. 3, line 22.

Various other heated liquid devices and methods of treating hollow organs or body orifices exist, and operate in the same basic manner. However, there is a need for a system and method for the creation of a localized therapeutic hyperthermia by means of a heated liquid directly contacting afflicted cells for a period of significant duration. More particularly there is a need for a device, or method of treatment, which involves, selecting a therapeutic liquid, heating the selected liquid through conduction so as to avoid EMF or ultrasonic radiation, placing a therapeutic applicator about the afflicted cells, and circulating the heated fluid through the therapeutic applicator, thereby creating a localized hyperthermia in the afflicted cells within the circumference of the applicator. Furthermore it would be beneficial to provide the use of a localized hyperthermic modality in conjunction with Vacuum Assisted Closure™, ("V.A.C.®") of open wounds. It is towards the fulfillment of these needs that the present invention is directed.

SUMMARY

The present invention is a novel device used to create a localized therapeutic effect on afflicted cells on an afflicted patient. These effects include cleaning, disinfecting, cooling, heating, and methods of use thereof. The device embodying the present invention comprises a therapeutic liquid, liquid supply means, liquid energizing means, circulating means, and control means. The device may also be used in conjunction with V.A.C.® therapy. These elements interact, and are employed, as briefly described below.

An appropriate therapeutic liquid is selected. Most often this liquid will be water, or a liquid comprising at least 90% water on a weight/weight ("w/w %") basis. Thermal energy is directly applied to, or taken from, the liquid. Most commonly the liquid will be heated. This energy transfer is regulated by the control means, which compares the actual liquid temperature with a selected reference temperature. The heated or cooled liquid is then used to create a local therapeutic effect. Control means also comprises system control means that monitors and regulates the overall operation of the device.

The balance of this description presumes that the liquid is heated rather than cooled. The liquid will either be recirculated if a closed loop embodiment is selected, or be used once and discarded if an open loop embodiment is selected. An afflicted area, such as a mole, skin cancer, or the like, is located on the afflicted patient. The afflicted area may be on the skin, or subcutaneous.

The circulation means comprises supply means, recovery means, and applicator means. The applicator has an open bottom or bottom portion and is placed about the afflicted cells on the skin of the patient, and most likely, some of the surrounding non-afflicted cells on the patent's skin as well. Before commencing the application of the therapeutic liquid, a fluid tight seal must be established between the patient and the application means; this seal must be maintained for at least the duration of the liquid application. The applicator may also comprise a fluid tight V.A.C.® dressing. The liquid flows from the liquid supply means, into the supply conduit of the circulation means, into the applicator means, and then into the return conduit. The liquid is then either recirculated, or discarded.

Circulation means also likely comprises liquid pressurization means that likely comprise a pump; though a sealed pressurized embodiment is also contemplated. Alternatively, gravity flow, or the negative pressure associated with V.A.C.®, roughly 150 mm Hg, in an open loop system could be considered. In a preferred embodiment, the pump is placed on the return side of the circulation means. This configuration has the advantage of applying negative pressure to the application means thereby creating a self actuated negative pressure seal between the application means and the patient's skin for the duration of therapeutic liquid application. Alternatively a sealing mechanism could be used to maintain the necessary seal between the application means and the afflicted patient. Applying pressure to the liquid also creates a more rapid circulation of the liquid to the epidermal region, which could have beneficial therapeutic effects.

Accordingly an object of the present invention is to provide a device that employs an exogenously heated fluid to provide direct thermotherapy to an afflicted potion of a patient.

Another object of the present invention is to provide localized thermal therapy where the perimeter of the afflicted portion of the patient is within the boundaries of the therapy applicator of the present invention.

A further object of the present invention is to provide a novel device that provides ravage to an afflicted patient.

Yet another object of the present invention is to combine the therapeutic effects of the present invention with the positive effects associated with V.A.C.®.

The foregoing has outlined some of the more pertinent objects of the present invention. These objects should be construed to be merely illustrative of some of the more prominent features and applications of the invention. Many other beneficial results can be attained by applying the disclosed invention in a different manner or by modifying the invention as will be described. Accordingly, other objects and a fuller understanding of the invention may be had by referring to the following Detailed Description of the Invention, which includes the preferred embodiment

BRIEF DESCRIPTION OF THE DRAWINGS

These and other features and advantages of the invention will now be described with reference to the drawings of certain preferred embodiments, which are intended to illustrate and not to limit the invention, and wherein like reference numbers refer to like components, and in which.

DETAILED DESCRIPTION

Figure 1:
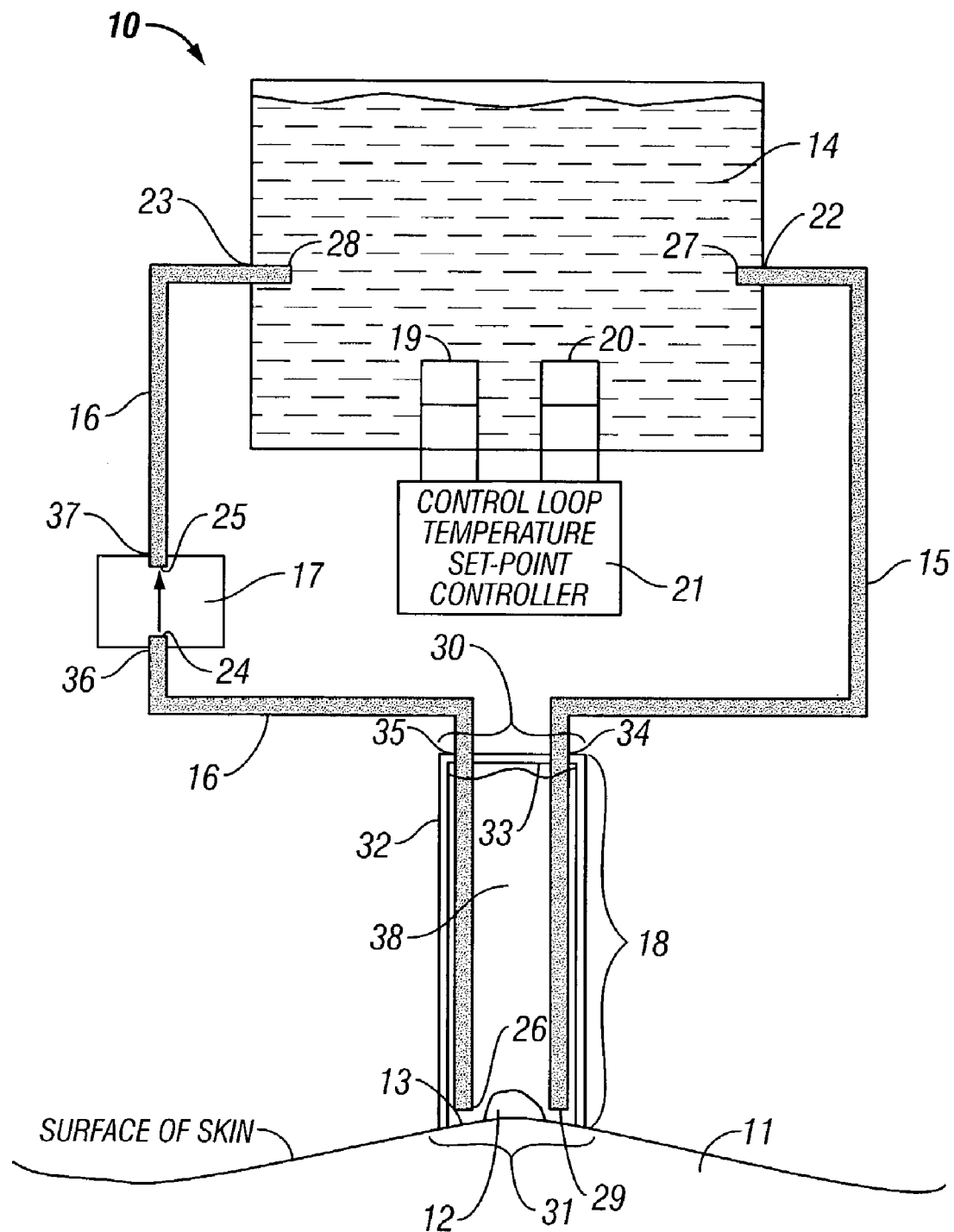
FIG. 1 is a block diagram illustrating a closed loop negative pressure embodiment that operates in accordance with the present invention.

Although those of ordinary skill in the art will readily recognize many alternative embodiments, especially in light of the illustrations provided herein, this detailed description is exemplary of the preferred embodiment of the present invention as well as alternate embodiments, the scope of which is limited only by the claims that may be drawn hereto.

The details of the preferred embodiments of the present invention are graphically and schematically illustrated in the accompanying drawings. Like elements in the drawings are represented by like numbers, and any similar elements are represented by like numbers with a different lower case letter suffix.

The preferred embodiments of the present invention, referred to throughout by the general reference 10, are intended to treat an afflicted patient 11, and particularly an afflicted area of the patient's skin 12, or the area immediately subcutaneous thereto, which is surrounded by a healthy area 13 of patient 11. As shown in FIGS. 1-8, the preferred embodiments 10, comprise a liquid storage means 14, a liquid supply means 15 terminated by ends 27 and 29, a liquid return means 16 terminated by ends 26, 36, 37, and 28, a liquid movement means 17, a therapy site liquid applicator means 18, a liquid heating means 19, a liquid temperature measuring means 20, and control means 21 which operatively coact in a manner more fully described below. The embodiments 10 are capable of creating a localized therapeutic hyerthermia, localized therapeutic hypothermia, lavage, irrigation, disinfection, or other therapeutic effects, either alone, or in conjunction with V.A.C.®.

Embodiment 10 may be used with a variety of liquids, in addition to water, and may provide either localized heating or localized cooling, in addition to direct contact effects from the liquid such as disinfection, irrigation, lavage, and so forth. However, to promote ease of understanding, the further description shall focus on the hyerthermia delivering embodiment using a liquid which on a w/w % basis is at least 90% water.

Figure 4:
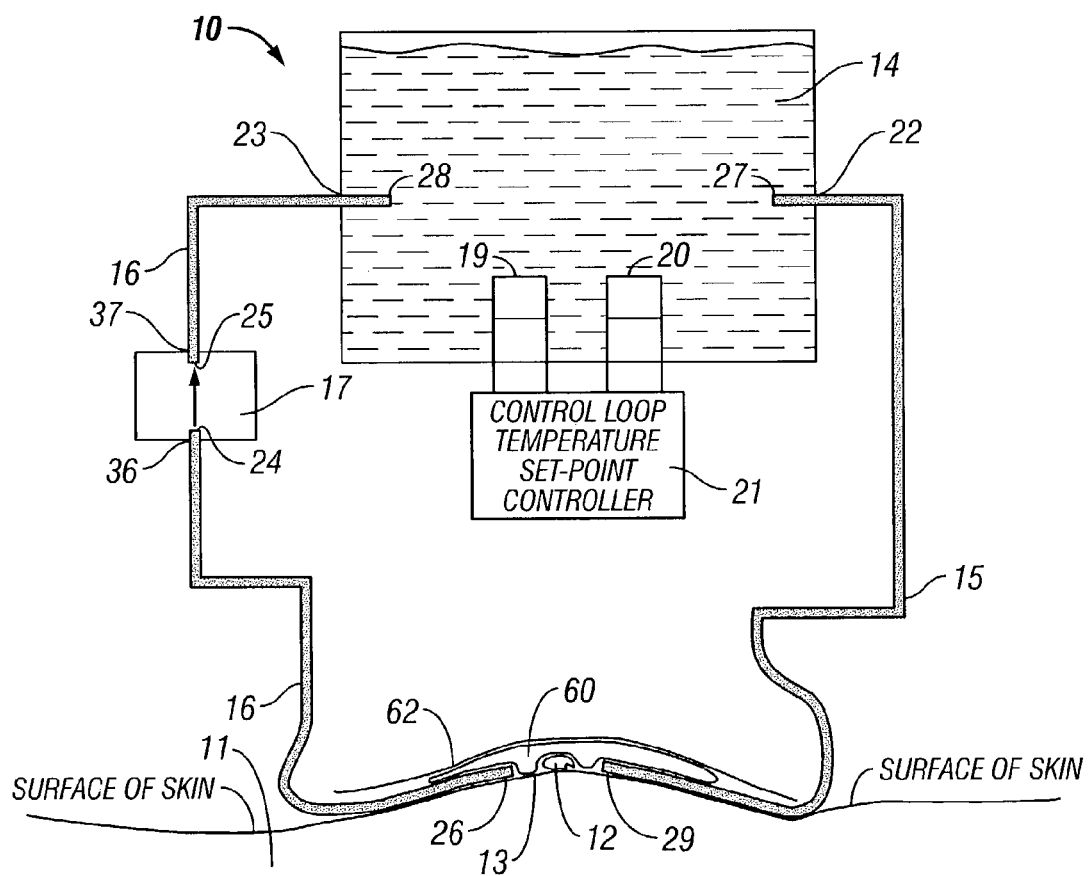
FIG. 4 is block diagram illustrating a closed loop negative pressure system embodiment, utilizing a V.A.C.® dressing, that operates in accordance with the present invention.
Figure 5:
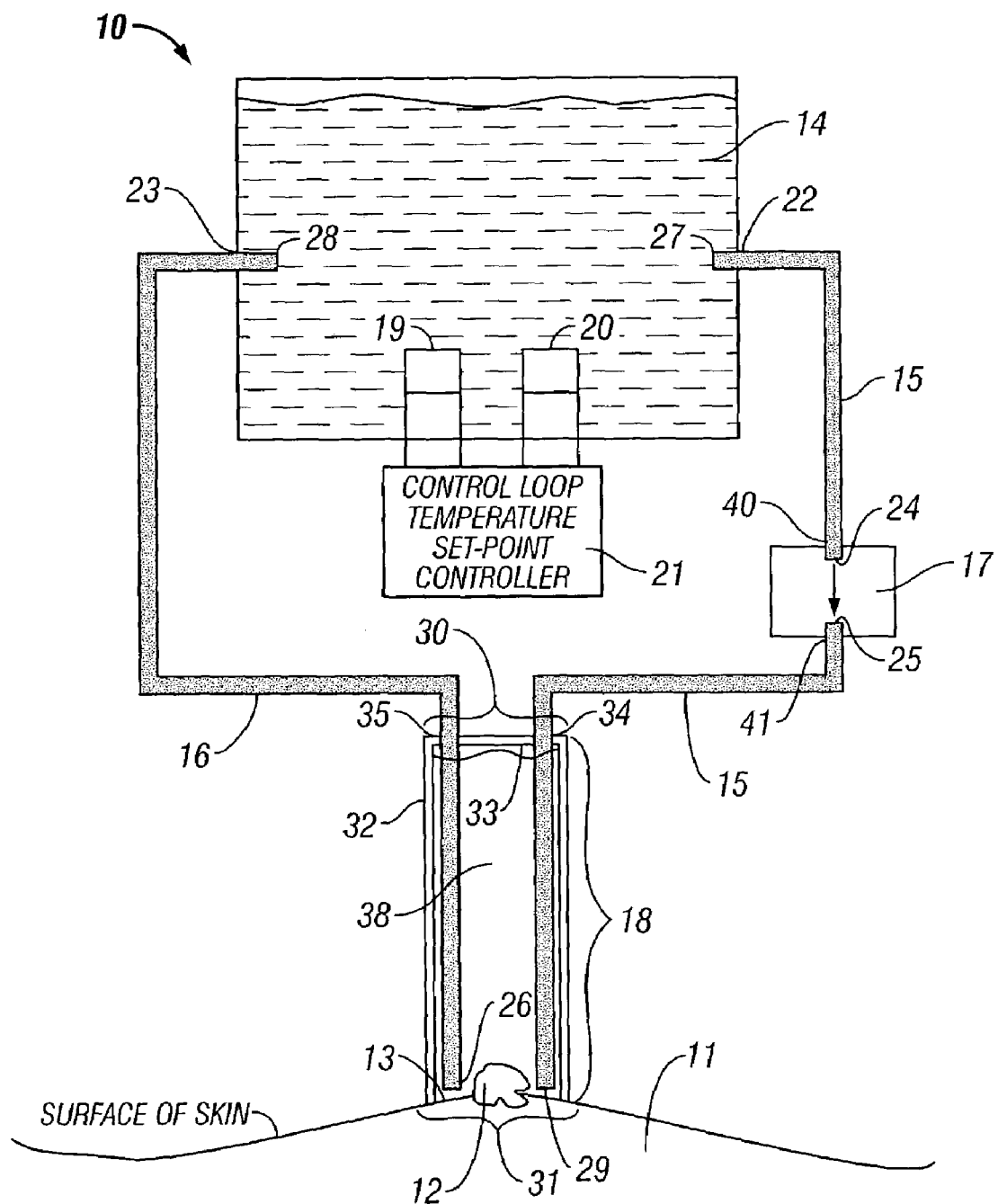
FIG. 5 is a block diagram illustrating a closed loop positive pressure system embodiment that operates in accordance with the present invention.

As shown in FIGS. 1, 4, and 5, liquid storage means 14, which most commonly comprises a reservoir, is operatively connected to both the liquid supply means 15, and to the liquid return means 16 so as to both provide liquid to liquid supply means 15 via outlet 22, and accept liquid from means 16 via inlet 23, as is more fully described below. Depending upon task dependent design choices, liquid storage means 14 may either be open, closed, or pressurized, so long as an adequate supply of liquid covers end 27 of supply means 15 when the embodiment 10 is in operation.

Control means 21 is connected to both liquid heating means 19 and liquid temperature measuring means 20 and coacts therewith in a manner more fully described below. Measuring means 20 may be located as necessary, depending upon both the speed of liquid flow, and the degree of temperature loss encountered. In a low speed flow embodiment, such as in FIG. 7, a location in proximity to end 29 may well be most desirable. Control means 21 receives temperature information from means 20 and, using this information, continuously regulates the power to heating means 19 in order to achieve the desired liquid temperature in a manner that is, at least in general, well known to those of ordinary skill in the art. Various control methods, including fuzzy logic, may be used to regulate the temperature of the liquid. The liquid temperature may be controlled to within 0.5° C. and possibly to within 0.1° C.

Figure 7:
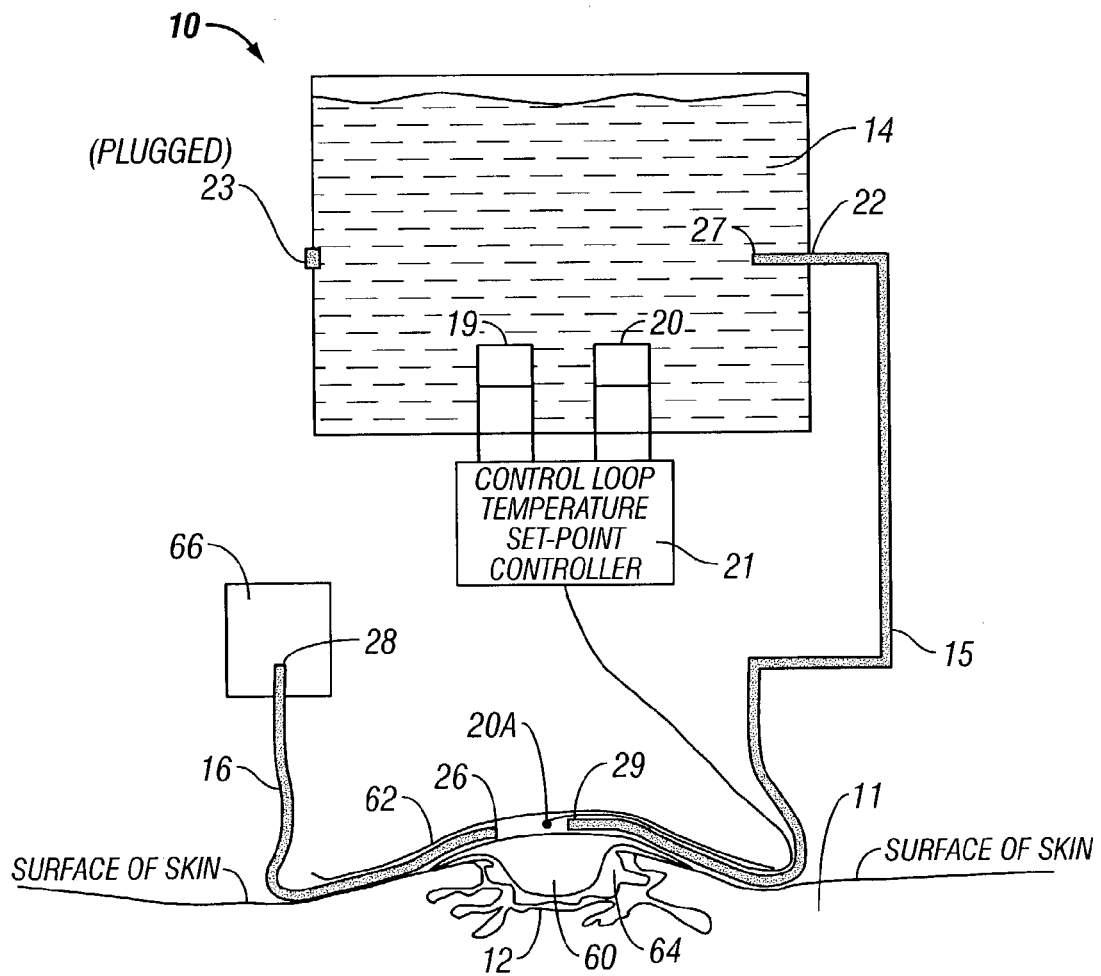
FIG. 7 is a block diagram illustrating an open loop negative pressure V.A.C.® embodiment that operates in accordance with the present invention.
Figure 8:
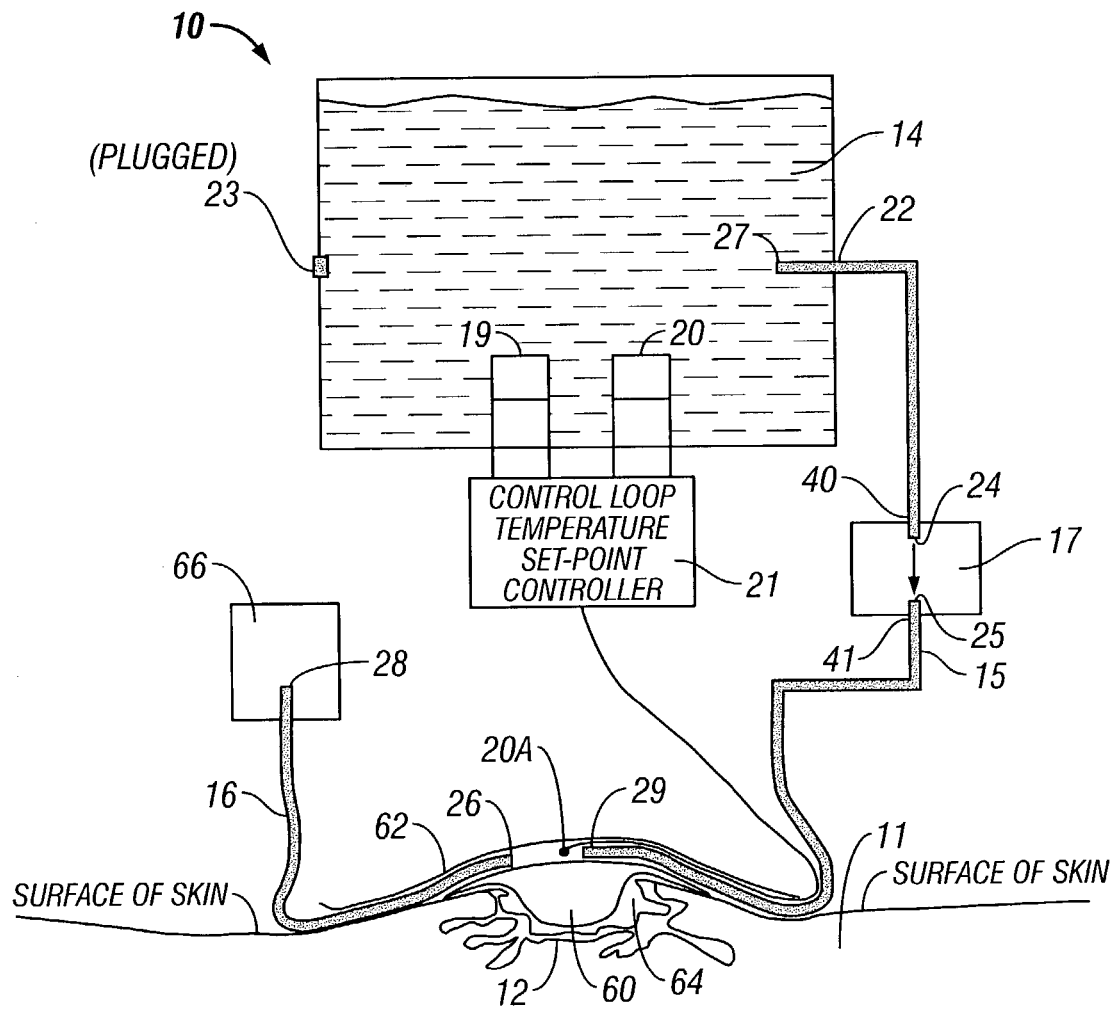
FIG. 8 is a block diagram illustrating a combined open loop negative pressure V.A.C.® and positive pressure pump system embodiment that operates in accordance with the present invention.

The precision heated liquid is delivered to the afflicted area 12 of patient 11 via liquid supply means 15, therapy site liquid applicator 18, liquid return means 16, and liquid movement means 17 all of which coact as described more fully below. Liquid movement means 17 generally comprises a pump of adequate capacity, as is well known in the art. Although the exact connection configuration of means 17 depends upon the overall system configuration of embodiment 10, in the presently preferred embodiment of embodiment 10, shown in FIG. 1, means 17 is operatively connected to liquid return means 16 via inlet 24 of means 17 and outlet 25 of means 17. This configuration supplies a negative pressure to applicator 18 because of the liquid it extracts therefrom. This negative pressure serves to hold applicator 18 in place about afflicted area 12 of afflicted patient 11 without the need for a separate engagement means being attached thereto. An alternative embodiment utilizing negative pressure is also shown in FIG. 7, where the V.A.C.® dressing adhesive covering 62, schematically represented in FIG. 3 coacts with dressing material 60 to perform the function of applicator 18, as is also shown in FIG. 8. The V.A.C.® embodiment would most likely be employed where afflicted cells comprise an open wound, such as is shown in FIGS. 7 and 8, where dressing material 60, coacts with dressing adhesive covering 62 to function as applicator 18 and covers wound 64 and also allows vacuum generated underneath dressing adhesive covering 62 to drain wound 64.

Figure 2:
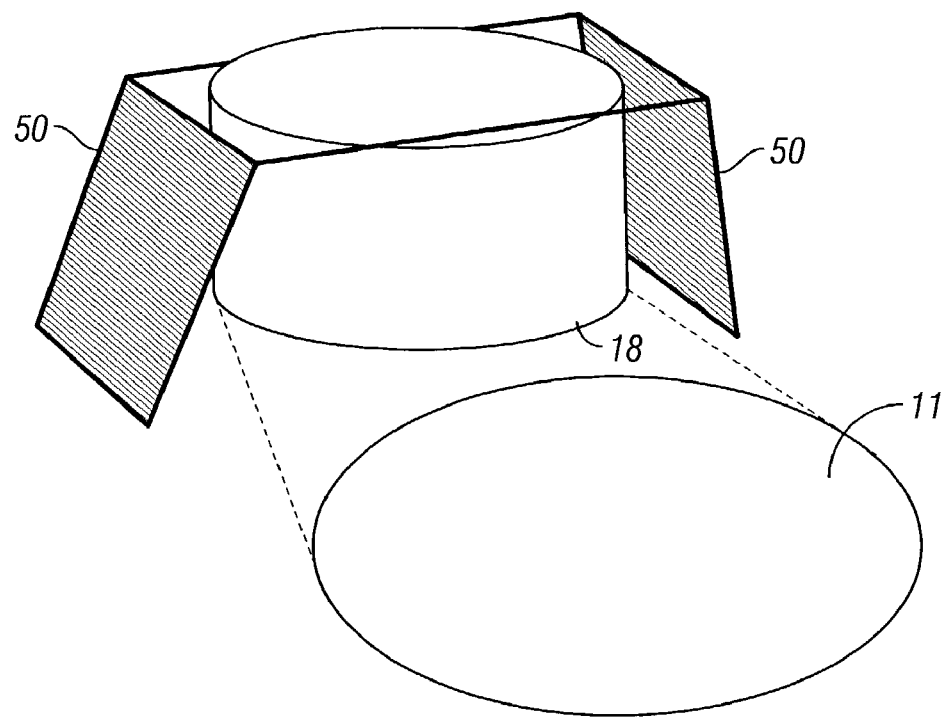
FIG. 2 is a perspective view of an applicator fastener that operates in accordance with the present invention.
Figure 3:
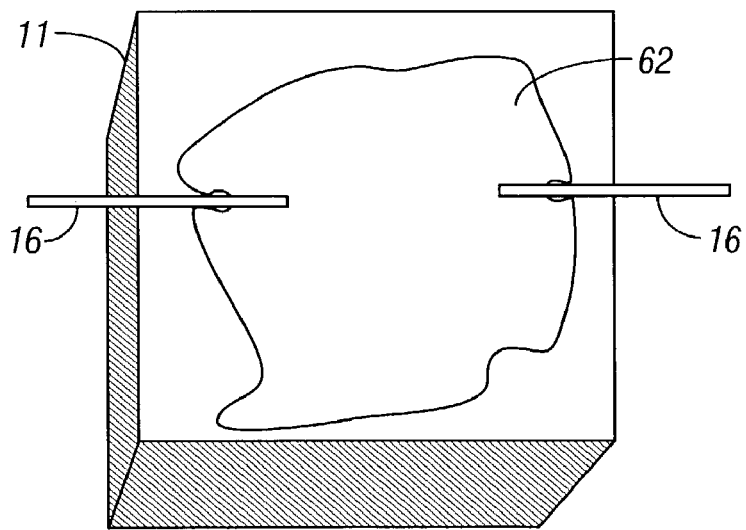
FIGS. 3 is a perspective view of a V.A.C.® dressing that operates in accordance with the present invention.
Figure 6:
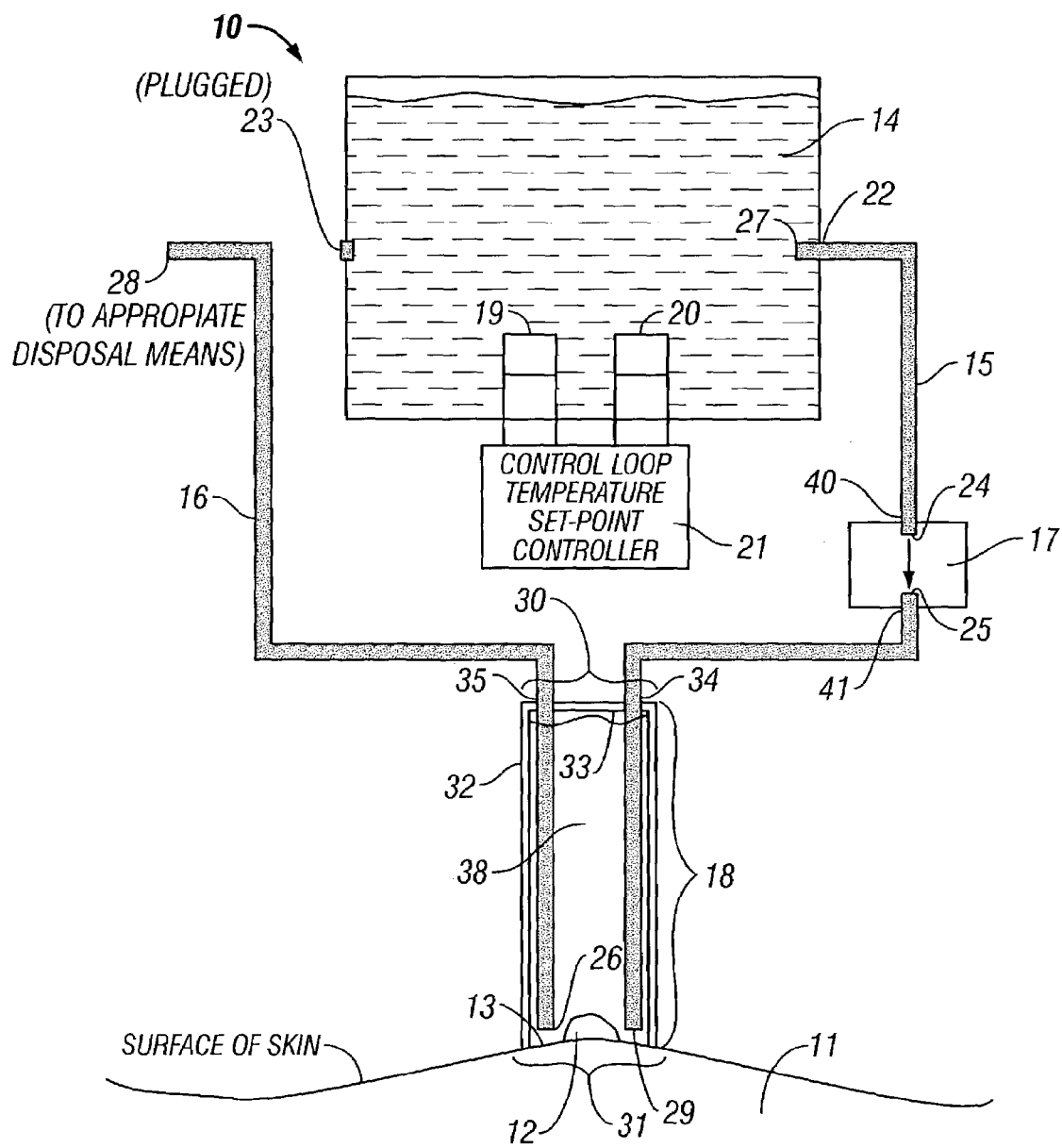
FIG. 6 is a block diagram illustrating an open loop positive pressure lavage system embodiment that operates in accordance with the present invention.

Some applications may require avoiding applying negative pressure to the afflicted area 12, by applying positive pressure as shown in FIGS. 5 and 6, thus alternate configurations could be used, such as shown in FIG. 2, where fastener 50 is depicted; plainly such fasteners are well known in the art, and any such known suitable fastener could be employed. The use of separate engagement means, such as fastener 50, to hold applicator 18 in place would avoid the need to apply negative pressure to afflicted area 12.

As shown in FIGS. 1, 4, 5, 6, and 8, a variety of alternate configurations of liquid movement means 17 could be used including configurations which would place means 17 at various positions along either liquid supply means 15, as shown in FIGS. 5 and 6, or liquid return means 16, as shown in FIGS. 1 and 4. In FIG. 7, negative pressure collection container 66 is used in lieu of liquid movement means 17 to move the fluid. As previously stated, the device in FIGS. 5 and 6 would require the use of fastener 50, whether the afflicted cells 12 were on the skin, or subcutaneous thereto. One alternative configuration (not shown) could place liquid movement means 17 inside reservoir 14 in a manner that would connect outlet 25 of liquid movement means 17 connected to end 27 of supply means 15. Alternatively, liquid movement means 17 could be placed inside reservoir 14 with inlet 24 of liquid movement means 17 connected to end 28 of return means 16. Alternative configurations, which would place liquid movement means 17 inside applicator 18, could also be used. Fastener 50 would be required if a positive pressure embodiment is employed.

Returning now to the specific embodiment shown in FIG. 1, liquid supply means 15 comprises supply end 27, delivery end 29, and a body portion intermediate these two ends. Applicator 18 comprises top 30, open bottom 31, outer surface 32, inner surface 33, liquid supply means receptor 34, and liquid return means receptor 35. Liquid return means comprise recovery end 26; pump intake end 36, pump output end 37, reservoir inlet end 28, every part of itself between end 26 and end 36, and every part of itself between end 37 and end 28. Liquid supply means 15, applicator 18, liquid return means 16, reservoir 14, and liquid movement/pressurization means 17 interconnect and coact in the following manner.

Supply end 27 of liquid supply means 15 is placed in liquid tight operative engagement with outlet 22 of reservoir 14. Delivery end 29 of liquid supply means 15 is placed in fluid tight engagement with applicator 18 via liquid supply means receptor 34 thereof. Applicator 18 is arranged about afflicted area 12 so that the inner surface 33 of open bottom 31 surrounds area 12, and most likely area 13, in fluid tight engagement. Cavity 38 is defined by inner surface 33, afflicted area 12, and the portion of area 13 surrounded by open bottom 31, as described above.

In this configuration pump 17 is placed between end 36 of liquid return line 16 and end 37 of liquid return line 16 in the following manner. End 26 of liquid return line 16 is placed in fluid tight engagement with liquid return means receptor 35. Pump intake end 36 of liquid return line 16 is placed in fluid tight engagement with pump intake 24. Any desired filtration means (not shown) could also logically be placed in proximity thereto. Pump output end 37 of liquid return means 16 is placed in fluid tight engagement with outlet 25 of pump 17. Reservoir inlet end 28 of liquid return means 16 is placed in fluid tight engagement with inlet 23 of reservoir 14.

The system control means regulate the overall operation of the embodiment 10, in a manner well known to those skilled in the art. Actuation means, timing means, data collection means, data recordation means, alarm means, and emergency shutoff means (all not shown) are just a few of the possible functions which could comprise the functions carried out by system control means. Existing data processing means remote from the location of the embodiment 10 could well perform some of these functions.

The embodiment 10 would be used in the following manner. The embodiment is connected to a power source (not shown) in reasonable proximity to the afflicted patient 11, convenient for attachment about afflicted area 12. If necessary, the control means are activated. A selected temperature is entered into set point controller 21. If desired, a selected duration is entered into the optional timing means. Any temperature or other alarm values are also entered into the system control means. Applicator 18 is placed about afflicted area 12. Embodiment 10 is activated. When the temperature of the liquid in reservoir 14 approximates the selected temperature set into controller 21, pump 17 is enabled. Upon actuation, pump 17 first partially evacuates cavity 38, thereby creating a negative pressure differential. This negative pressure acts to hold applicator 18 in place about afflicted area 12. Heated liquid then exists reservoir 14 through outlet end 27 of liquid supply means 15, and passes through supply conduit liquid supply means 15, enters applicator 18, comes into contact with afflicted area 12, transfers heat to afflicted area 12, and exits applicator 18 into liquid return means 16. This liquid passes through the pump 17 and is returned into reservoir 14 through inlet end 28 of liquid return means 16, thereby completing the loop.

Certain advantages may accrue from moving the heated liquid rapidly through the embodiment. These advantages are believed to include better temperature control, a faster rate of heat transfer to the afflicted cells, a quicker attainment of thermal equilibrium, and a lower requirement for total system liquid. It is also anticipated that this device and modality would also be effective in treating cells subcutaneous the skin areas 12 and 13, placed within the open bottom 31 of applicator 18.

Additionally, an open loop system, as shown in FIG. 6, where fluid comes into contact with skin areas 12, 13, and is then either discarded, in a manner well known in the art, or is placed in storage for later disposal, in a manner well known in the art, could be used for irrigation therapy, lavage, or the like. As is apparent to one of ordinary skill in the art, this apparatus would well serve this purpose if an open loop system were to be used, and a positive, rather than a negative pressure pump is provided. In that case, an additional mechanism to hold applicator 18 in place, fastener 50, would be required, as the pump would be operatively connected with liquid supply means 15 rather than liquid return means 16. Fluid supply means would supply either a limited quantity of fluid, such as from reservoir 14, or an unlimited source of fluid from a faucet or the like.

An additional embodiment would be to use a mild oxidizing agent as the fluid in this device. Such an agent, were it to have a greater affect upon afflicted cells, than non-afflicted cells, would provide an enhanced therapeutic effect in conjunction with the therapy herein described. An example of such a solution would be 3% Hydrogen peroxide, U.S.P. Likely a more benign disinfecting solution would be used, such as are well known to those skilled in the art, for irrigation or other treatment of wounds.

While the invention has been described herein with reference to certain preferred embodiments, theses embodiments have been presented by way of example only, and not to limit the scope of the invention. Many other variations are possible, which would be obvious to one skilled in the art. Accordingly, the scope of the invention should be identified only in accordance with the claims that follow.

We claim:

1. A device for applying therapeutic liquid to an afflicted area of a surface of an afflicted patient's body, comprising:
   a supply means for supplying a therapeutic liquid;
   a return means for returning liquid;
   a control means for thermally regulating the therapeutic liquid;
   a negative pressure pump operatively coupled to said return means;
   an applicator interposed between said supply means and said return means, said applicator being adapted to be secured about said afflicted area;
   wherein the applicator comprises a dressing material for placement on the afflicted area and a dressing adhesive covering; and
   wherein the negative pressure pump is fluidly connected to the supply means such that liquid is returned to the supply means after being drawn through the applicator.

2. The device according to claim 1 further comprising a reservoir for storing said therapeutic liquid.

3. The device according to claim 1, wherein the liquid is heated prior to application to the afflicted area.

4. The device according to claim 3, wherein heated liquid induces a localized hyperthermia in the afflicted area after application of the heated liquid to the afflicted area.

5. The device according to claim 1, wherein the liquid is cooled prior to application to the afflicted area.

6. The device according to claim 5, wherein the cooled liquid induces a localized hypothermia in the afflicted area after application of the cooled liquid to the afflicted area.

7. The device according to claim 1, wherein negative pressure generated by the negative pressure pump underneath the dressing adhesive covering functions to drain the afflicted-area, to secure the dressing material against the afflicted area, and to provide negative pressure wound therapy to the afflicted area.

8. The apparatus of claim 1, wherein the applicator further comprises a porous pad.

9. An apparatus for applying therapeutic liquid, the apparatus comprising:
a reservoir;
a controller operably connected to the reservoir to regulate a temperature of liquid stored in the reservoir;
an applicator fluidly connected to the reservoir;
a negative pressure pump fluidly connected to the applicator to draw liquid from the reservoir through the applicator;
wherein the applicator further comprises a dressing and an adhesive covering; and
wherein the negative pressure pump is fluidly connected to the reservoir such that liquid is returned to the reservoir after being drawn through the applicator.

10. The apparatus of claim 9, further comprising a liquid heater exposed to liquid and operably connected to the controller, wherein the controller is operable to regulate power to the liquid heater so that liquid is heated.

11. The apparatus according to claim 10, wherein:
the applicator is adapted to be positioned about an afflicted area; and
the heated liquid induces a localized hyperthermia in the afflicted area after application of the heated liquid to the afflicted area.

12. The apparatus of claim 9, wherein the applicator further comprises a porous pad.

13. The apparatus of claim 9, wherein:
the applicator is adapted to be positioned about an afflicted area; and
the liquid is cooled prior to application to the afflicted area.

14. An apparatus for applying therapeutic liquid, the apparatus comprising:
a reservoir;
an applicator;
a supply line fluidly connected to the reservoir and the applicator;
a negative pressure pump;
a return line fluidly connected to the applicator and the negative pressure pump;
a set-point controller operably coupled to the reservoir to regulate a temperature of therapeutic liquid stored in the reservoir;
wherein the negative pressure pump is operable to draw liquid from the reservoir through the applicator;
wherein the applicator further comprises a dressing and an adhesive covering; and
wherein the negative pressure pump is fluidly connected to the reservoir such that liquid is returned to the reservoir after being drawn through the applicator.

15. The apparatus of claim 14, further comprising a liquid heater exposed to liquid and operably connected to the set-point controller, wherein the set-point controller is operable to regulate power to the liquid heater so that liquid is heated.

16. An apparatus for applying therapeutic liquid, the apparatus comprising:
a reservoir;
an applicator;
a supply line fluidly connected to the reservoir and the applicator;
a negative pressure pump;
a return line fluidly connected to the applicator and the negative pressure pump;
a set-point controller operably coupled to the reservoir to regulate a temperature of therapeutic liquid stored in the reservoir;
wherein the negative pressure pump is operable to draw liquid from the reservoir through the applicator;
wherein the applicator comprises a top surface, a wall surface, an open bottom, and a receptor; and
wherein the supply line is coupled to the receptor.

17. The apparatus of claim 16, wherein the negative pressure pump is fluidly connected to the reservoir such that liquid is returned to the reservoir after being drawn through the applicator.

18. The apparatus of claim 16, further comprising a liquid heater exposed to liquid and operably connected to the set-point controller, wherein the set-point controller is operable to regulate power to the liquid heater so that liquid is heated.

19. A method of creating localized therapeutic hyperthermia, the method comprising:
applying heat to a liquid;
placing an applicator over an afflicted area;
applying a negative pressure to the applicator to provide an engagement between the applicator and the afflicted area and to draw the liquid through the applicator; and
recirculating the liquid through the applicator after the liquid has been drawn through the applicator; and
wherein the applicator includes a dressing and an adhesive covering.

20. The method of claim 19, further comprising:
measuring a temperature of the liquid; and
adjusting the heat applied to the liquid to maintain the liquid at a therapeutically beneficial temperature.

* * * * *